United States Patent
Bond et al.

(10) Patent No.: US 6,746,766 B2
(45) Date of Patent: *Jun. 8, 2004

(54) MULTICOMPONENT FIBERS COMPRISING STARCH AND POLYMERS

(75) Inventors: Eric Bryan Bond, Maineville, OH (US); Jean-Philippe Marie Autran, Wyoming, OH (US); Larry Neil Mackey, Fairfield, OH (US); Isao Noda, Fairfield, OH (US); Hugh Joseph O'Donnell, Cincinnati, OH (US); Dean Van Phan, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/294,417

(22) Filed: Nov. 14, 2002

(65) Prior Publication Data

US 2003/0104204 A1 Jun. 5, 2003

Related U.S. Application Data

(63) Continuation-in-part of application No. 09/853,131, filed on May 10, 2001, now abandoned.

(51) Int. Cl.[7] .................................................. D01F 8/00
(52) U.S. Cl. ..................... 428/370; 428/373; 428/374; 428/372
(58) Field of Search ................ 428/373, 370, 428/374, 372

(56) References Cited

U.S. PATENT DOCUMENTS

| | | | |
|---|---|---|---|
| 4,139,699 A | 2/1979 | Hernandez et al. | |
| 4,853,168 A | 8/1989 | Eden et al. | |

(List continued on next page.)

FOREIGN PATENT DOCUMENTS

| | | |
|---|---|---|
| EP | 1 035 163 A2 | 9/2000 |
| EP | 1 035 239 A2 | 9/2000 |
| EP | 1217106 A1 | 6/2002 |
| EP | 1217107 A1 | 6/2002 |
| GB | 1 247 474 | 9/1971 |
| JP | 62-28410 | 2/1987 |
| JP | 04100913 | 4/1992 |
| JP | 96027627 A | 1/1996 |
| JP | 97041224 | 2/1997 |
| JP | 9276331 | 10/1997 |
| JP | 1008364 | 1/1998 |
| WO | WO 01/46506 A2 | 6/2001 |
| WO | WO 01/48078 A1 | 7/2001 |
| WO | WO 01/49912 A1 | 7/2001 |

OTHER PUBLICATIONS

Fringant, C., et al., "Preparation of Mixed Esters of Starch or Use of an External Plasticizer: Two Different Ways to Change the Properties of Starch Acetate Films", Carbohydrate Polymers 35 (1998) 97–106, Elsevier Science, Ltd.

Glenn, G. M., et al., "Starch, Fiber and $CaCO_3$ Effects on the Physical Properties of Foams Made by a Baking Process," Industrial Crops and Products 14 (2001) 201–212, Elsevier Science, Ltd.

Jandura, P., et al., "Thermal Degradation Behavior of Cellulose Fibers Partially Esterified with Some Long Chain Organic Acids", Polymer Degradation and Stability 70 (2000) 387–394, Elsevier Science, Ltd.

Primary Examiner—N. Edwards
(74) Attorney, Agent, or Firm—Leonard W. Lewis; Angela Marie Stone

(57) ABSTRACT

The present invention is directed to multicomponent fibers. The fibers may be in a side-by-side, sheath-core, segmented pie, islands-in-the-sea configuration, or any combination of configurations. Each component of the fiber will comprise destructurized starch and/or a thermoplastic polymer. The present invention is also directed to nonwoven webs and disposable articles comprising the multicomponent fibers. The nonwoven webs may also contain other synthetic or natural fibers blended with the multicomponent fibers of the present invention.

8 Claims, 5 Drawing Sheets

U.S. PATENT DOCUMENTS

| | | |
|---|---|---|
| 5,316,578 A | 5/1994 | Buehler et al. |
| 5,417,679 A | 5/1995 | Toms et al. |
| 5,422,387 A | 6/1995 | Toms et al. |
| 5,425,987 A | 6/1995 | Shawver et al. |
| 5,516,815 A | 5/1996 | Buehler et al. |
| 5,593,768 A | 1/1997 | Gessner |
| 5,593,778 A | 1/1997 | Kondo et al. |
| 5,703,160 A | 12/1997 | Dehennau et al. |
| 5,814,404 A | 9/1998 | Rutherford et al. |
| 5,851,937 A | 12/1998 | Wu et al. |
| 5,874,486 A | 2/1999 | Bastioli et al. |
| 5,945,480 A | 8/1999 | Wang et al. |
| 5,985,776 A | 11/1999 | Bertrand et al. |
| 6,045,908 A | 4/2000 | Nakajima et al. |
| 6,096,809 A | 8/2000 | Lorcks et al. |
| 6,117,925 A | 9/2000 | Tomka |
| 6,218,321 B1 | 4/2001 | Lorcks et al. |
| 6,376,072 B1 | 4/2002 | Evans et al. |
| 6,451,170 B1 | 9/2002 | Anderson et al. |

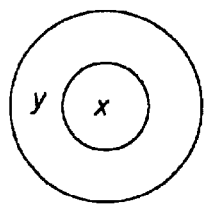
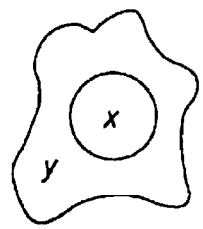
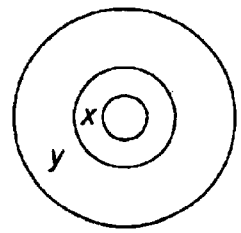
Fig. 1A     Fig. 1B     Fig. 1C
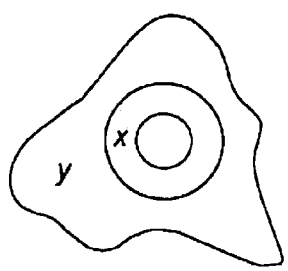
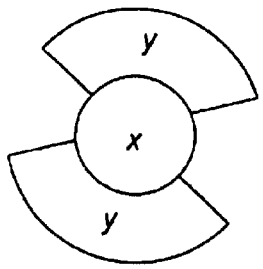
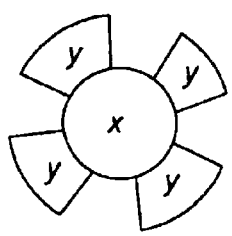
Fig. 1D     Fig. 1E     Fig. 1F
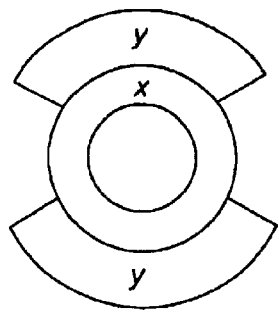
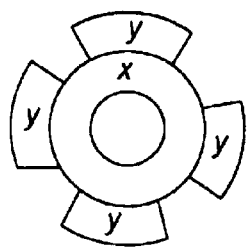
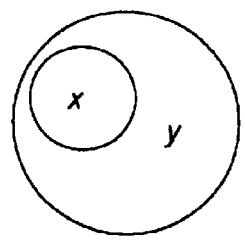
Fig. 1G     Fig. 1H     Fig. 1I

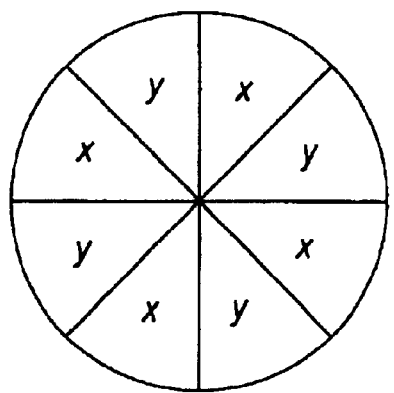
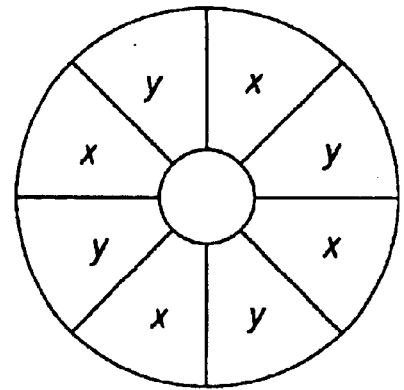
Fig. 2A　　　　　　　　Fig. 2B
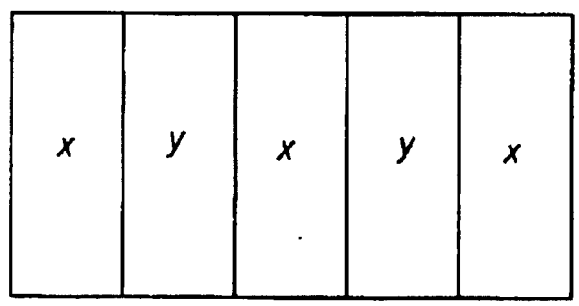
Fig. 3

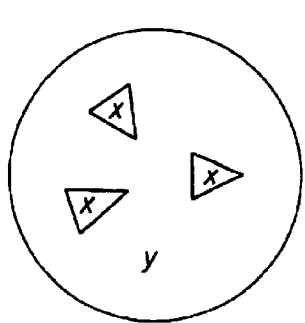
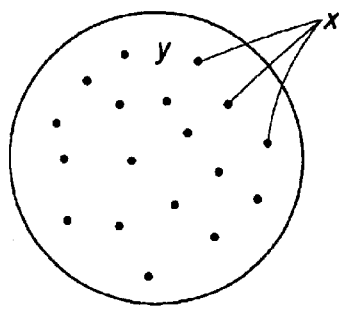
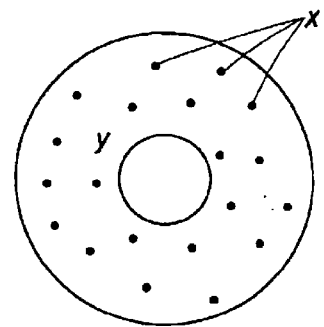
Fig. 5A          Fig. 5B          Fig. 5C
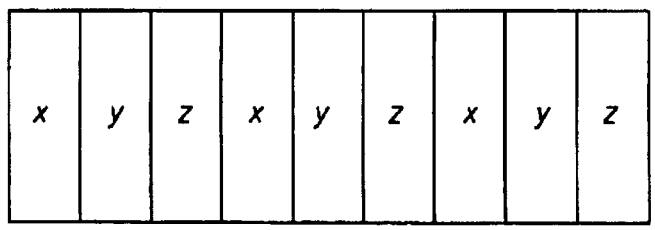
Fig. 6

MULTICOMPONENT FIBERS COMPRISING STARCH AND POLYMERS

CROSS REFERENCE TO RELATED PATENTS

This application is a continuation-in-part and claims priority to commonly owned U.S. applications Ser. No. 09/853,131, filed May 10, 2001 now abandoned.

FIELD OF THE INVENTION

The present invention relates to multicomponent fibers comprising starch and polymers and specific configurations of the fibers. The fibers are used to make nonwoven webs and disposable articles.

BACKGROUND OF THE INVENTION

There have been many attempts to make nonwoven articles. However, because of costs, the difficultly in processing, and end-use properties, there are only a limited number of options. Many compositions have limited processability.

Useful fibers for nonwoven article are difficult to produce and pose additional challenges compared to films and laminates. This is because the material and processing characteristics for fibers is much more stringent than for producing films, blow-molding articles, and injection-molding articles. For the production of fibers, the processing time during structure formation is typically much shorter and flow characteristics are more demanding on the material's physical and rheological characteristics. The local strain rate and shear rate are much greater in fiber production than other processes. Additionally, a homogeneous composition is required for fiber spinning. For spinning very fine fibers, small defects, slight inconsistencies, or non-homogeneity in the melt are not acceptable for a commercially viable process.

Attempts have been made to process natural starch on standard equipment and existing technology known in the plastic industry. Fibers comprising starch are desired as the starch is environmentally degradable. Since natural starch generally has a granular structure, it needs to be "destructurized" before it can be melt processed into fine denier filaments. Modified starch (alone or as the major component of a blend) has been found to have poor melt extensibility resulting in difficulty in successfully production of fibers, films, foams or the like. Additionally, starch fibers are difficult to spin and are virtually unusable to make nonwovens due to the low tensile strength, stickiness, and the inability to be bonded to form nonwovens.

To produce fibers that have more acceptable processability and end-use properties, thermoplastic polymers need to be combined with starch. Selection of a suitable polymer that is acceptable for blending with starch is challenging. The polymer must have good spinning properties and a suitable melting temperature. The melting temperature must be high enough for end-use stability to prevent melting or structural deformation, but not too high of a melting temperature to be able to be processable with starch without burning the starch. These requirements make selection of a thermoplastic polymer to produce starch-containing multicomponent fibers very difficult.

Consequently, there is a need for a cost-effective and easily processable multicomponent fibers made of natural starches and thermoplastic polymers. Moreover, the starch and polymer composition should be suitable for use in commercially available equipment used to make the multicomponent fibers. There is also a need for disposable, nonwoven articles made from these multicomponent fibers.

SUMMARY OF THE INVENTION

The present invention is directed to multicomponent fibers. The configuration of the multicomponent fibers may be side-by-side, sheath-core, segmented pie, islands-in-the-sea, or any combination of configurations. Each component of the fiber will comprise destructurized starch and/or a thermoplastic polymer.

The present invention is also directed to nonwoven webs and disposable articles comprising the multicomponent fibers. The nonwoven webs may also contain other synthetic or natural fibers blended with the multicomponent fibers of the present invention.

BRIEF DESCRIPTION OF THE DRAWINGS

These and other features, aspects and advantages of the present invention will become better understood with regard to the following description, appended claims, and accompanying drawings where:

FIG. 1 is schematic drawings illustrating a cross-sectional view of a bicomponent fiber having a sheath-core configuration.

FIG. 2 is schematic drawings illustrating a cross-sectional view of a bicomponent fiber having a segmented pie configuration.

FIG. 3 is schematic drawing illustrating a cross-sectional view of a bicomponent fiber having a ribbon configuration.

FIG. 5 is schematic drawings illustrating a cross-sectional view of a bicomponent fiber having an islands-in-the-sea configuration.

FIG. 6 is schematic drawing illustrating a cross-sectional view of a tricomponent fiber having a ribbon configuration.

DETAILED DESCRIPTION OF THE INVENTION

Figure 4A:
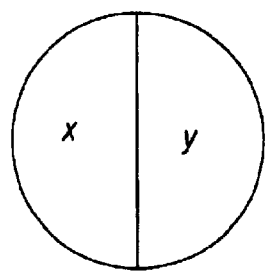
FIG. 4 is schematic drawings illustrating a cross-sectional view of a bicomponent fiber having a side-by-side configuration.

All percentages, ratios and proportions used herein are by weight percent of the composition, unless otherwise specified. The Examples are given in parts of the total composition. All average values are calculated "by weight" of the composition or components thereof, unless otherwise expressly indicated. "Average molecular weight", or "molecular weight" for polymers, unless otherwise indicated, refers to number average molecular weight. Number average molecular weight, unless otherwise specified, is determined by gel permeation chromatography. All patents or other publications cited herein are incorporated herein by reference with respect to all text contained therein for the purposes for which the reference was cited. Inclusion of any such patents or publications is not intended to be an admission that the cited reference is citable as prior art or that the subject matter therein is material prior art against the present invention. The compositions, products, and processes described herein may comprise, consist essentially of, or consist of any or all of the required and/or optional components, ingredients, compositions, or steps described herein.

The specification contains a detailed description of (1) materials of the present invention, (2) configuration of the multicomponent fibers, (3) material properties of the multicomponent fibers, (4) processes, and (5) articles.

(1) Materials

Starch

The present invention relates to the use of starch, a low cost naturally occurring polymer. The starch used in the present invention is destructurized starch, which is necessary for adequate spinning performance and fiber properties. The term "thermoplastic starch" is used to mean destructured starch with a plasticizer.

Since natural starch generally has a granular structure, it needs to be destructurized before it can be melt processed and spun like a thermoplastic material. For gelatinization, the starch can be destructurized in the presence of a solvent which acts as a plasticizer. The solvent and starch mixture is heated, typically under pressurized conditions and shear to accelerate the gelatinization process. Chemical or enzymatic agents may also be used to destructurize, oxidize, or derivatize the starch. Commonly, starch is destructurized by dissolving the starch in water. Fully destructured starch results when no lumps impacting the fiber spinning process are present.

Suitable naturally occurring starches can include, but are not limited to, corn starch, potato starch, sweet potato starch, wheat starch, sago palm starch, tapioca starch, rice starch, soybean starch, arrow root starch, bracken starch, lotus starch, cassava starch, waxy maize starch, high amylose corn starch, and commercial amylose powder. Blends of starch may also be used. Though all starches are useful herein, the present invention is most commonly practiced with natural starches derived from agricultural sources, which offer the advantages of being abundant in supply, easily replenishable and inexpensive in price. Naturally occurring starches, particularly corn starch, wheat starch, and waxy maize starch, are the preferred starch polymers of choice due to their economy and availability.

Modified starch may also be used. Modified starch is defined as non-substituted or substituted starch that has had its native molecular weight characteristics changed (i.e. the molecular weight is changed but no other changes are necessarily made to the starch). If modified starch is desired, chemical modifications of starch typically include acid or alkali hydrolysis and oxidative chain scission to reduce molecular weight and molecular weight distribution. Natural, unmodified starch generally has a very high average molecular weight and a broad molecular weight distribution (e.g. natural corn starch has an average molecular weight of up to about 60,000,000 grams/mole (g/mol)). The average molecular weight of starch can be reduced to the desirable range for the present invention by acid reduction, oxidation reduction, enzymatic reduction, hydrolysis (acid or alkaline catalyzed), physical/mechanical degradation (e.g., via the thermomechanical energy input of the processing equipment), or combinations thereof. The thermomechanical method and the oxidation method offer an additional advantage when carried out in situ. The exact chemical nature of the starch and molecular weight reduction method is not critical as long as the average molecular weight is in an acceptable range. Ranges of number average molecular weight for starch or starch blends added to the melt can be from about 3,000 g/mol to about 8,000,000 g/mol, preferably from about 10,000 g/mol to about 5,000,000 g/mol, preferably from about 10,000 to about 2,000,000 g/mol, more preferably from about 20,000 g/mol to about 3,000,000 g/mol. In other embodiments, the average molecular weight is otherwise within the above ranges but about 1,000,000 or less, or about 700,000 or less.

Although not required, substituted starch can be used. If substituted starch is desired, chemical modifications of starch typically include etherification and esterification. Substituted starches may be desired for better compatibility or miscibility with the thermoplastic polymer and plasticizer. However, this must be balanced with the reduction in the rate of degradability. The degree of substitution of the chemically substituted starch is from about 0.01 to 3.0. A low degree of substitution, 0.01 to 0.06, may be preferred.

Typically, the composition comprises from about 1% to about 99%, preferably from about 10% to about 85%, more preferably from about 20% to about 75%, and most preferably from about 40% to about 60%, of the starch and polymer composition or of the total fiber. Alternatively, the thermoplastic starch (starch combined with a plasticizer) may comprise up to 100% of one component of the multicomponent fiber with this component not containing any thermoplastic polymer. The weight of starch in the composition includes starch and its naturally occurring bound water content. The term "bound water" means the water found naturally occurring in starch and before mixing of starch with other components to make the composition of the present invention. The term "free water" means the water that is added in making the composition of the present invention. A person of ordinary skill in the art would recognize that once the components are mixed in a composition, water can no longer be distinguished by its origin. The starch typically has a bound water content of about 5% to 16% by weight of starch. It is known that additional free water may be incorporated as the polar solvent or plasticizer, and not included in the weight of the starch.

Thermoplastic Polymers

Thermoplastic polymers which are substantially compatible with starch are also required in the present invention. As used herein, the term "substantially compatible" means when heated to a temperature above the softening and/or the melting temperature of the composition, the polymer is capable of forming a substantially homogeneous mixture with the starch after mixing with shear or extension. The thermoplastic polymer used must be able to flow upon heating to form a processable melt and resolidify as a result of crystallization or vitrification.

The polymer must have a melting temperature sufficiently low to prevent significant degradation of the starch during compounding and yet be sufficiently high for thermal stability during use of the fiber. Suitable melting temperatures of polymers are from about 80° to about 190° C. and preferably from about 90° to about 180° C. Thermoplastic polymers having a melting temperature above 190° C. may be used if plasticizers or diluents are used to lower the observed melting temperature. In one aspect of the present invention, it may be desired to use a thermoplastic polymer having a glass transition temperature of less than 0° C. Polymers having this low glass transition temperature include polypropylene, polyethylene, polyvinyl alcohol, ethylene acrylic acid, and others.

The polymer must have a rheological characteristics suitable for melt spinning. The molecular weight of the polymer must be sufficiently high to enable entanglement between polymer molecules and yet low enough to be melt spinnable. For melt spinning, biodegradable thermoplastic polymers can have molecular weights below 500,000 g/mol, preferably from about 5,000 g/mol to about 400,000 g/mol, more preferable from about 5,000 g/mol to about 300,000 g/mol and most preferably from about 100,000 g/mol to about 200,000 g/mol.

The thermoplastic polymers must be able to solidify fairly rapidly, preferably under extensional flow, and form a thermally stable fiber structure, as typically encountered in known processes as staple fibers (spin draw process) or spunbond continuous filament process. Suitable thermoplastic polymers include polypropylene and copolymers of polypropylene, polyethylene and copolymers of polyethylene, polyamides and copolymers of polyamides, polyesters and copolymers of polyesters, and mixtures thereof. Other suitable polymers include polyamides such as Nylon 6, Nylon 11, Nylon 12, Nylon 46, Nylon 66, polyvinyl acetates, polyethylene/vinyl acetate copolymers, polyethylene/methacrylic acid copolymers, polystyrene/methyl methacrylate copolymers, polymethyl methacrylates, polyethylene terephalates, low density polyethylenes, linear low density polyethylenes, ultra low density polyethylenes, high density polyethylene, and combinations thereof. Other nonlimiting examples of polymers include atactic polypropylene, polybutylene, polycarbonates, poly(oxymethylene), styrene copolymers, polyetherimide, poly(vinyl acetate), poly(methacrylate), poly sulfone, polyolefin carboxylic acid copolymers such as ethylene acrylic acid copolymer, ethylene maleic acid copolymer, ethylene methacrylic acid copolymer, and ethylene acrylic acid copolymer, and combinations thereof. Other suitable polymers include acid substituted vinyl polymers such as ethylene acrylic acid which is commercially available as PRIMACOR by Dow. The polymers disclosed in U.S. Pat. No. 5,593,768 to Gessner are herein incorporated by reference. Preferred thermoplastic polymers include polypropylene, polyethylene, polyamides, polyvinyl alcohol, ethylene acrylic acid, polyolefin carboxylic acid copolymers, polyesters, and combinations thereof.

Depending upon the specific polymer used, the process, and the final use of the fiber, more than one polymer may be desired. The thermoplastic polymers of the present invention is present in an amount to improve the mechanical properties of the fiber, improve the processability of the melt, and improve attenuation of the fiber. The selection of the polymer and amount of polymer will also determine if the fiber is thermally bondable and effect the softness and texture of the final product. Typically, when present in the starch and polymer blend, the thermoplastic polymers are present in an amount of from about 1% to about 99%, preferably from about 10% to about 80%, more preferably from about 30% to about 70%, and most preferably from about 40% to about 60%, by weight of the fiber. Alternatively, one component of the multicomponent fiber may contain up to 100% of one or more thermoplastic polymer with this component not containing any starch.

Plasticizer

A plasticizer can be used in the present invention to destructurize the starch and enable the starch to flow, i.e. create a thermoplastic starch. The same plasticizer may be used to increase melt processability or two separate plasticizers may be used. The plasticizers may also improve the flexibility of the final products, which is believed to be due to the lowering of the glass transition temperature of the composition by the plasticizer. The plasticizers should preferably be substantially compatible with the polymeric components of the present invention so that the plasticizers may effectively modify the properties of the composition. As used herein, the term "substantially compatible" means when heated to a temperature above the softening and/or the melting temperature of the composition, the plasticizer is capable of forming a substantially homogeneous mixture with starch.

An additional plasticizer or diluent for the thermoplastic polymer may be present to lower the polymer's melting temperature and improve overall compatibility with the thermoplastic starch blend. Furthermore, thermoplastic polymers with higher melting temperatures may be used if plasticizers or diluents are present which suppress the melting temperature of the polymer. The plasticizer will typically have a molecular weight of less than about 100,000 g/mol and may preferably be a block or random copolymer or terpolymer where one or more of the chemical species is compatible with another plasticizer, starch, polymer, or combinations thereof.

Nonlimiting examples of useful hydroxyl plasticizers include sugars such as glucose, sucrose, fructose, raffinose, maltodextrose, galactose, xylose, maltose, lactose, mannose erythrose, glycerol, and pentaerythritol; sugar alcohols such as erythritol, xylitol, malitol, mannitol and sorbitol; polyols such as ethylene glycol, propylene glycol, dipropylene glycol, butylene glycol, hexane triol, and the like, and polymers thereof; and mixtures thereof. Also useful herein as hydroxyl plasticizers are poloxomers and poloxamines. Also suitable for use herein are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers are phthalate esters, dimethyl and diethylsuccinate and related esters, glycerol triacetate, glycerol mono and diacetates, glycerol mono, di, and triprpionates, butanoates, stearates, lactic acid esters, citric acid esters, adipic acid esters, stearic acid esters, oleic acid esters, and other father acid esters which are biodegradable. Aliphatic acids such as ethylene acrylic acid, ethylene maleic acid, butadiene acrylic acid, butadiene maleic acid, propylene acrylic acid, propylene maleic acid, and other hydrocarbon based acids. All of the plasticizers may be use alone or in mixtures thereof. A low molecular weight plasticizer is preferred. Suitable molecular weights are less than about 20,000 g/mol, preferably less than about 5,000 g/mol and more preferably less than about 1,000 g/mol.

Preferred plasticizers include glycerin, mannitol, and sorbitol, with sorbitol being the most preferred. The amount of plasticizer is dependent upon the molecular weight, amount of starch, and the affinity of the plasticizer for the starch. Generally, the amount of plasticizer increases with increasing molecular weight of starch. Typically, the plasticizer present in the final multicomponent fiber composition comprises from about 2% to about 90%, more preferably from about 5% to about 70%, most preferably from about 10% to about 50%. The plasticizer may be present in one or more of the components.

Optional Materials

Optionally, other ingredients may be incorporated into the spinnable starch composition. These optional ingredients may be present in quantities of less than about 50%, preferably from about 0.1% to about 20%, and more preferably from about 0.1% to about 12% by weight of the composition. The optional materials may be used to modify the processability and/or to modify physical properties such as elasticity, tensile strength and modulus of the final product. Other benefits include, but are not limited to, stability including oxidative stability, brightness, color, flexibility, resiliency, workability, processing aids, viscosity modifiers, and odor control. Nonlimiting examples include salts, slip agents, crystallization accelerators or retarders, odor masking agents, cross-linking agents, emulsifiers, surfactants, cyclodextrins, lubricants, other processing aids, optical brighteners, antioxidants, flame retardants, dyes, pigments, fillers, proteins and their alkali salts, waxes, tackifying resins, extenders, and mixtures thereof. Slip agents may be used to help reduce the tackiness or coefficient of friction in the fiber. Also, slip agents may be used to improve fiber stability, particularly in high humidity or temperatures. A suitable slip agent is polyethylene. A salt may also be added to the melt. The salt may help to solubilize the starch, reduce discoloration, make the fiber more water responsive, or used as a processing aid. A salt will also function to help reduce the solubility of a binder so it does not dissolve, but when put in water or flushed, the salt will dissolve then enabling the binder to dissolve and create a more aqueous responsive product. Nonlimiting examples of salts include sodium chloride, potassium chloride, sodium sulfate, ammonium sulfate and mixtures thereof.

Other additives are typically included with the starch polymer as a processing aid and to modify physical properties such as elasticity, dry tensile strength, and wet strength of the extruded fibers. Suitable extenders for use herein include gelatin, vegetable proteins such as sunflower protein, soybean proteins, cotton seed proteins, and water soluble polysaccharides; such as alginates, carrageenans, guar gum, agar, gum arabic and related gums, pectin, water soluble derivatives of cellulose, such as alkylcelluloses, hydroxyalkylcelluloses, and carboxymethylcellulose. Also, water soluble synthetic polymers, such as polyacrylic acids, polyacrylic acid esters, polyvinylacetates, polyvinylalcohols, and polyvinylpyrrolidone, may be used.

Lubricant compounds may further be added to improve the flow properties of the starch material during the processes used for producing the present invention. The lubricant compounds can include animal or vegetable fats, preferably in their hydrogenated form, especially those which are solid at room temperature. Additional lubricant materials include mono-glycerides and di-glycerides and phosphatides, especially lecithin. For the present invention, a preferred lubricant compound includes the monoglyceride, glycerol mono-stearate.

Further additives including inorganic fillers such as the oxides of magnesium, aluminum, silicon, and titanium may be added as inexpensive fillers or processing aides. Other inorganic materials include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, may be used as processing aides. Other optional materials that modify the water responsiveness of the thermoplastic starch blend fiber are stearate based salts, such as sodium, magnesium, calcium, and other stearates, and rosin components including anchor gum rosin. Another material that can be added is a chemical composition formulated to accelerate the environmental degradation process such as colbalt stearate, citric acid, calcium oxide, and other chemical compositions found in U.S. Pat. No. 5,854,304 to Garcia et al., herein incorporated by reference in its entirety.

Other additives may be desirable depending upon the particular end use of the product contemplated. For example, in products such as toilet tissue, disposable towels, facial tissues and other similar products, wet strength is a desirable attribute. Thus, it is often desirable to add to the starch polymer cross-linking agents known in the art as "wet strength" resins. A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. Polyamide-epichlorohydrin resins are cationic polyamide amine-epichlorohydrin wet strength resins which have been found to be of particular utility. Glyoxylated polyacrylamide resins have also been found to be of utility as wet strength resins.

It is found that when suitable cross-linking agent such as Parez® is added to the starch composition of the present invention under acidic condition, the composition is rendered water insoluble. Still other water-soluble cationic resins finding utility in this invention are urea formaldehyde and melamine formaldehyde resins. The more common functional groups of these polyfunctional resins are nitrogen containing groups such as amino groups and methyl groups attached to nitrogen. Polyethylenimine type resins may also find utility in the present invention. For the present invention, a suitable cross-linking agent is added to the composition in quantities ranging from about 0.1% by weight to about 10% by weight, more preferably from about 0.1% by weight to about 3% by weight. The starch and polymers in the fibers of the present invention may be chemically associated. The chemical association may be a natural consequence of the polymer chemistry or may be engineered by selection of particular materials. This is most likely to occur if a cross-linking agent is present. The chemical association may be observed by changes in molecular weight, NMR signals, or other methods known in the art. Advantages of chemical association include improved water sensitivity, reduced tackiness, and improved mechanical properties, among others.

Other polymers, such as rapidly biodegradable polymers, may also be used in the present invention depending upon final use of the fiber, processing, and degradation or flushability required. Polyesters containing aliphatic components are suitable biodegradable thermoplastic polymers. Among the polyesters, ester polycondensates containing aliphatic constituents and poly(hydroxycarboxylic) acid are preferred. The ester polycondensates include diacids/diol aliphatic polyesters such as polybutylene succinate, polybutylene succinate co-adipate, aliphatic/aromatic polyesters such as terpolymers made of butylenes diol, adipic acid and terephtalic acid. The poly(hydroxycarboxylic) acids include lacid acid based homopolymers and copolymers, polyhydroxybutyrate, or other polyhydroxyalkanoate homopolymers and copolymers. Preferred is a homopolymer or copolymer of poly lactic acid having a melting temperature from about 160° to about 175° C. Modified poly lactic acid and different stero configurations may also be used. Preferably, molecular weights of from about 4,000 g/mol to about 400,000 g/mol are found for the poly lactic acid.

An example of a suitable commercially available poly lactic acid is NATUREWORKS from Cargill Dow and LACEA from Mitsui Chemical. An example of a suitable commercially available diacid/diol aliphatic polyester is the polybutylene succinate/adipate copolymers sold as BIONOLLE 1000 and BIONOLLE 3000 from the Showa Highpolmer Company, Ltd. Located in Tokyo, Japan. An example of a suitable commercially available aliphatic/aromatic copolyester is the poly(tetramethylene adipate-coterephthalate) sold as EASTAR BIO Copolyester from Eastman Chemical or ECOFLEX from BASF. The amount of biodegradable polymers will be from about 0.1% to about 40% by weight of the fiber.

Although starch is the preferred natural polymer in the present invention, a protein-based polymer could also be used. Suitable protein-based polymers include soy protein, zein protein, and combinations thereof. The protein-based polymer may be present in an amount of from about 1% to about 80% and preferably from about 1% to about 60%.

After the fiber is formed, the fiber may further be treated or the bonded fabric can be treated. A hydrophilic or hydrophobic finish can be added to adjust the surface energy and chemical nature of the fabric. For example, fibers that are hydrophobic may be treated with wetting agents to facilitate absorption of aqueous liquids. A bonded fabric can also be treated with a topical solution containing surfactants, pigments, slip agents, salt, or other materials to further adjust the surface properties of the fiber.

(2) Configuration

The multiconstituent fibers of the present invention may be in many different configurations. Constituent, as used herein, is defined as meaning the chemical species of matter or the material. Multiconstituent fiber, as used herein, is defined to mean a fiber containing more than one chemical species or material. Generally, fibers may be of monocomponent or multicomponent in configuration. Component, as used herein, is defined as a separate part of the fiber that has a spatial relationship to another part of the fiber. The term multicomponent, as used herein, is defined as a fiber having more than one separate part in spatial relationship to one another. The term multicomponent includes bicomponent, which is defined as a fiber having two separate parts in a spatial relationship to one another. The different components of multicomponent fibers are arranged in substantially distinct regions across the cross-section of the fiber and extend continuously along the length of the fiber.

Spunbond structures, staple fibers, hollow fibers, shaped fibers, such as multi-lobal fibers and multicomponent fibers can all be produced by using the compositions and methods of the present invention. The bicomponent and multicomponent fibers may be in a side-by-side, sheath-core, segmented pie, ribbon, islands-in-the-sea configuration, or any combination thereof. The sheath may be continuous or non-continuous around the core. The ratio of the weight of the sheath to the core is from about 5:95 to about 95:5. The fibers of the present invention may have different geometries that include round, elliptical, star shaped, rectangular, and other various eccentricities.

The fibers of the present invention may also be splittable fibers. Rheological, thermal, and solidification differential behavior can potentially cause splitting. Splitting may also occur by a mechanical means such as ringrolling, stress or strain, use of an abrasive, or differential stretching, and/or by fluid induced distortion, such as hydrodynamic or aerodynamic.

A plurality of microfibrils may also result from the present invention. The microfibrils are very fine fibers contained within a multi-constituent monocomponent or multicomponent extrudate. The plurality of polymer microfibrils have a cable-like morphological structure and longitudinally extend within the fiber, which is along the fiber axis. To enable the microfibrils to be formed in the present invention, a sufficient amount of polymer is required to generate a co-continuous phase morphology such that the polymer microfibrils are formed in the starch matrix. Typically, greater than 15%, preferably from about 15% to about 90%, more preferably from about 25% to about 80%, and more preferably from about 35% to about 70% of polymer is desired. A "co-continuous phase morphology" is found when the microfibrils are substantially longer than the diameter of the fiber. Microfibrils are typically from about 0.1 micrometers to about 10 micrometers in diameter while the fiber typically has a diameter of from about (10 times the microfibril) 10 micrometers to about 50 micrometers. In addition to the amount of polymer, the molecular weight of the thermoplastic polymer must be high enough to induce sufficient entanglement to form microfibrils. The preferred molecular weight is from about 10,000 to about 500,000 g/mol. The formation of the microfibrils also demonstrates that the resulting fiber is not homogeneous, but rather that polymer microfibrils are formed within the starch matrix. The microfibrils comprised of the degradable polymer will mechanically reinforce the fiber to improve the overall tensile strength and make the fiber thermally bondable. Alternatively, microfibrils can be obtained by co-spinning starch and polymer melt without phase mixing, as in an islands-in-a-sea bicomponent configuration. In an islands-in-a-sea configuration, there may be several hundred fine fibers present.

There are many different combinations for the multicomponent fibers of the present invention. A starch/polymer blend may be both the sheath and the core with one of the components containing more starch or polymer than the other component. The starch in the starch/polymer blend may be in any suitable amount depending upon desired use of the multicomponent fiber. Alternatively, the starch/polymer blend may be the sheath with the core being pure polymer or starch. The starch/polymer composition could also be the core with the sheath being pure polymer or starch. For example, a bicomponent fibers with a core of pure starch and the sheath containing either pure polymer or a starch/polymer blend may be desired where the fibers are used in a thermal bonding process. This configuration allows for high biodegradability and low cost due to the high content of starch, but the fiber is still thermally bondable.

The present invention may have any variations on the bicomponent fibers in a sheath-core configuration. For example, the core or sheath may contain microfibrils. The sheath may be continuous or noncontinuous around the core. The sheath-core configuration may also be found in multicomponent fibers. There may be more than one sheath surrounding the core. For example, an inner sheath may surround the core with an outer sheath surrounding the inner sheath. Alternatively, the core could have an islands-in-the-sea configuration or a segmented pie.

The exact configuration of the multicomponent fiber desired is dependent upon the use of the fiber. A major advantage of the multicomponent fiber compared to the monocomponent fiber is that there is spatial control over the placement of the starch and/or polymer in the fiber. This is advantageous for enabling thermal bonding, reducing stickiness of the starch, and other resulting properties of the fiber. A preferred configuration is a bicomponent fiber with starch contained in the core and the thermoplastic polymer in the sheath. This configuration will help the starch to have improved long term stability by protecting the starch from aging, discoloration, mold, an other things in the environment. Also, this particular configuration will reduce the potential stickiness of the feel of the starch and allow for the fiber to be easily thermally bondable. The multicomponent fibers can be used as a whole fiber or the starch can be removed to only use the thermoplastic polymer. The starch can be removed through bonding methods, hydrodynamic entanglement, post-treatment such as mechanical deformation, or dissolving in water. The fibers having the starch removed may be used in nonwoven articles that are desired to be extra soft and/or have better barrier properties. Additionally, because starch is an inexpensive material, the starch and polymer fibers with the starch removed will be a more cost-effective fiber.

FIG. 1 is schematic drawings illustrating a cross-sectional view of a bicomponent fiber having a sheath-core configuration. Components X and Y may be a thermoplastic starch, a thermoplastic polymer, or a blend of the starch and polymer.

FIG. 1A illustrates a concentric sheath-core configuration with Component X comprising the solid core and Component Y comprising the continuous sheath.

FIG. 1B illustrates a sheath-core configuration with Component X comprising the solid core and Component Y comprising the shaped continuous sheath.

FIG. 1C illustrates a sheath-core configuration with Component X comprising the hollow core and Component Y comprising the continuous sheath.

FIG. 1D illustrates a sheath-core configuration with Component X comprising the hollow core and Component Y comprising the shaped continuous sheath.

FIG. 1E illustrates a sheath-core configuration with Component X comprising the solid core and Component Y comprising the discontinuous sheath.

FIG. 1F illustrates a sheath-core configuration with Component X comprising the solid core and Component Y comprising the discontinuous sheath.

FIG. 1G illustrates a sheath-core configuration with Component X comprising the hollow core and Component Y comprising the discontinuous sheath.

FIG. 1H illustrates a sheath-core configuration with Component X comprising the hollow core and Component Y comprising the discontinuous sheath.

FIG. 1I illustrates an eccentric sheath-core configuration with Component X comprising the solid core and Component Y comprising the continuous sheath.

FIG. 2 is schematic drawings illustrating a cross-sectional view of a bicomponent fiber having a segmented pie configuration. Components X and Y may be a thermoplastic starch, a thermoplastic polymer, or a blend of the starch and polymer.

FIG. 2A illustrates a solid eight segmented pie configuration.

FIG. 2B illustrates a hollow eight segmented pie configuration. This configuration is a suitable configuration for producing splittable fibers.

FIG. 3 is schematic drawing illustrating a cross-sectional view of a bicomponent fiber having a ribbon configuration. Components X and Y may be a thermoplastic starch, a thermoplastic polymer, or a blend of the starch and polymer.

FIG. 4 is schematic drawings illustrating a cross-sectional view of a bicomponent fiber having a side-by-side configuration. Components X and Y may be a thermoplastic starch, a thermoplastic polymer, or a blend of the starch and polymer.

FIG. 4A illustrates a side-by-side configuration.

Figure 4B:
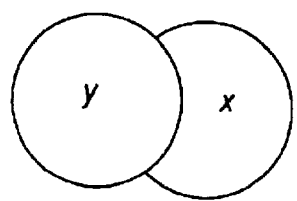

FIG. 4B illustrates a side-by-side configuration with a rounded adjoining line. The adjoining line is where two components meet. Component Y is present in a higher amount than Component X.

Figure 4C:
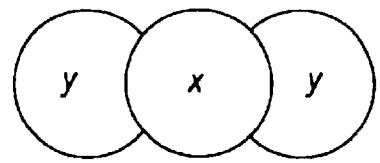

FIG. 4C is a side-by-side configuration with Component Y being positioned on either side of Component X with a rounded adjoining line.

Figure 4D:
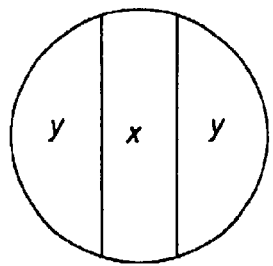

FIG. 4D is a side-by-side configuration with Component Y being positioned on either side of Component X.

Figure 4E:
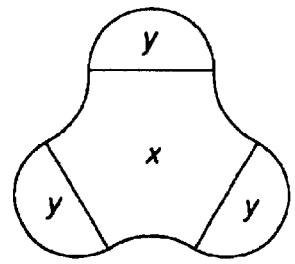

FIG. 4E is a shaped side-by-side configuration with Component Y being positioned on the tips of Component X.

FIG. 5 is schematic drawings illustrating a cross-sectional view of a bicomponent fiber having an islands-in-the-sea configuration. Components X and Y may be athermoplastic starch, a thermoplastic polymer, or a blend of the starch and polymer.

FIG. 5A is a solid islands-in the-sea configuration with Component X being surrounded by Component Y. Component X is triangular in shape.

FIG. 5B is a solid islands-in the-sea configuration with Component X being surrounded by Component Y.

FIG. 5C is a hollow islands-in the-sea configuration with Component X being surrounded by Component Y.

FIG. 6 is schematic drawing illustrating a cross-sectional view of a tricomponent fiber having a ribbon configuration. Components X, Y, and Z may be a thermoplastic starch, a thermoplastic polymer, or a blend of the starch and polymer.

Figure 7:
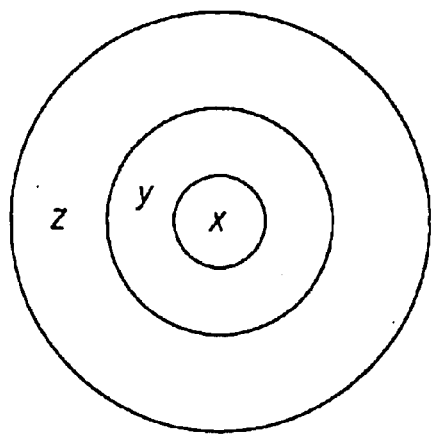
FIG. 7 is schematic drawing illustrating a cross-sectional view of a tricomponent fiber having a concentric sheath-core configuration.

FIG. 7 is schematic drawing illustrating a cross-sectional view of a tricomponent fiber having a concentric sheath-core configuration with Component X comprising the solid core, Component Y comprising the inside continuous sheath, and Component Z comprising the outside continuous sheath. Components X, Y, and Z may be a thermoplastic starch, a thermoplastic polymer, or a blend of the starch and polymer.

Figure 8:
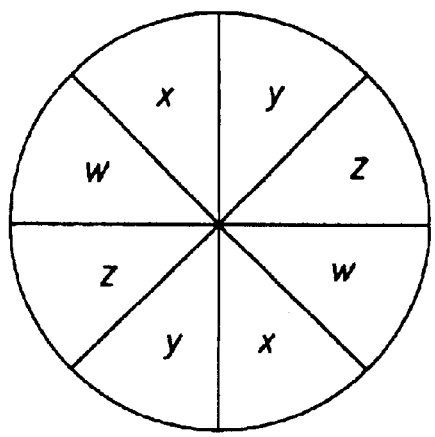
FIG. 8 is schematic drawing illustrating a cross-sectional view of a multicomponent fiber having a eight segmented pie configuration.

FIG. 8 is schematic drawing illustrating a cross-sectional view of a multicomponent fiber having a solid eight segmented pie configuration. Components X, Y, Z, and W may be a thermoplastic starch, a thermoplastic polymer, or a blend of the starch and polymer.

Figure 9:
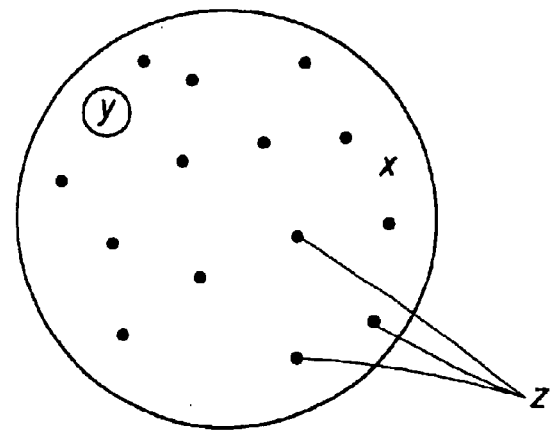
FIG. 9 is a schematic drawing illustrating a cross-sectional view of a tricomponent fiber having an islands-in-the-sea configuration.

FIG. 9 is a schematic drawing illustrating a cross-sectional view of a tricomponent fiber having a solid islands-in-the-sea configuration. Component X surrounds the single island comprising Component Y and the plurality of islands comprising Component Z. Components X, Y, and Z may be a thermoplastic starch, a thermoplastic polymer, or a blend of the starch and polymer.

(3) Material Properties

A "highly attenuated fiber" is defined as a fiber having a high draw down ratio. The total fiber draw down ratio is defined as the ratio of the fiber at its maximum diameter (which is typically results immediately after exiting the capillary) to the final fiber diameter in its end use. The total fiber draw down ratio via either staple, spunbond, or melt-blown process will be greater than 1.5, preferable greater than 5, more preferably greater than 10, and most preferably greater than 12. This is necessary to achieve the tactile properties and useful mechanical properties.

Preferably, the highly attenuated multicomponent fiber will have a diameter of less than 200 micrometers. More preferably the fiber diameter will be 100 micrometer or less, even more preferably 50 micrometers or less, and most preferably less than 30 micrometers. Fibers commonly used to make nonwovens will have a diameter of from about 5 micrometers to about 30 micrometers. Fiber diameter is controlled by spinning speed, mass through-put, and blend composition. The fibers produced in the present invention are environmentally degradable.

The multicomponent fibers produced in the present invention may be environmentally degradable depending upon the amount of starch that is present and the specific configuration of the fiber. The starch contained in the fibers of the present invention will be environmentally degradable. "Environmentally degradable" is defined being biodegradable, disintigratable, dispersible, flushable, or compostable or a combination thereof. In the present invention, the multicomponent fibers, nonwoven webs, and articles may be environmentally degradable. As a result, the fibers may be easily and safely disposed of either in existing composting facilities or may be flushable and can be safely flushed down the drain without detrimental consequences to existing sewage infrastructure systems. The flushability of the multicomponent fibers of the present invention when used in disposable products such as wipes and feminine hygiene items offer additional convenience and discretion to the consumer.

Biodegradable is defined as meaning when the matter is exposed to an aerobic and/or anaerobic environment, the ultimate fate is eventually reduction to monomeric components due to microbial, hydrolytic, and/or chemical actions. Under aerobic conditions, biodegradation leads to the transformation of the material into end products such as carbon dioxide and water. Under anaerobic conditions, biodegradation leads to the transformation of the materials into carbon dioxide, water, and methane. The biodegradability process is often described as mineralization. Biodegradability means that all organic constituents of the fibers are subject to decomposition eventually through biological activity.

There are a variety of different standardized biodegradability methods that have been established over time by various organization and in different countries. Although the tests vary in the specific testing conditions, assessment methods, and criteria desired, there is reasonable convergence between different protocols so that they are likely to lead to similar conclusions for most materials. For aerobic biodegrability, the American Society for Testing and Materials (ASTM) has established ASTM D 5338-92: Test methods for Determining Aerobic Biodegradation of Plastic Materials Under Controlled Composting Conditions. The test measures the percent of test material that mineralizes as a function of time by monitoring the amount of carbon dioxide being released as a result of assimilation by microorganisms in the presence of active compost held at a thermophilic temperature of 58° C. Carbon dioxide production testing may be conducted via electrolytic respirometry. Other standard protocols, such 301B from the Organization for Economic Cooperation and Development (OECD), may also be used. Standard biodegradation tests in the absence of oxygen are described in various protocols such as ASTM D 5511-94. These tests are used to simulate the biodegradability of materials in an anaerobic solid-waste treatment facility or sanitary landfill. However, these conditions are less relevant for the type of disposable applications that are described for the fibers and nonwovens in the present invention. The multicomponent fibers of the present invention may be biodegradable.

Disintegration occurs when the fibrous substrate has the ability to rapidly fragment and break down into fractions small enough not to be distinguishable after screening when composted or to cause drainpipe clogging when flushed. A disintegradable material will also be flushable. Most protocols for disintegradability measure the weight loss of test materials over time when exposed to various matrices. Both aerobic and anaerobic disintegration tests are used. Weight loss is determined by the amount of fibrous test material that is no longer collected on an 18 mesh sieve with 1 millimeter openings after the materials is exposed to wastewater and sludge. For disintegration, the difference in the weight of the initial sample and the dried weight of the sample recovered on a screen will determine the rate and extent of disintegration. The testing for biodegradability and disintegration are very similar as a very similar environment, or the same environment, will be used for testing. To determine disintegration, the weight of the material remaining is measured while for biodegradability, the evolved gases are measured. The fibers of the present invention may rapidly disintegrate.

The fibers of the present invention may also be compostable. ASTM has developed test methods and specifications for compostability. The test measures three characteristics: biodegradability, disintegration, and lack of ecotoxicity. Tests to measure biodegradability and disintegration are described above. To meet the biodegradability criteria for compostability, the material must achieve at least about 60% conversion to carbon dioxide within 40 days. For the disintegration criteria, the material must have less than 10% of the test material remain on a 2 millimeter screen in the actual shape and thickness that it would have in the disposed product. To determine the last criteria, lack of ecotoxicity, the biodegradation byproducts must not exhibit a negative impact on seed germination and plant growth. One test for this criteria is detailed in OECD 208. The International Biodegradable Products Institute will issue a logo for compostability once a product is verified to meet ASTM 6400-99 specifications. The protocol follows Germany's DIN 54900 which determine the maximum thickness of any material that allows complete decomposition within one composting cycle.

The multicomponent fibers described herein are typically used to make disposable nonwoven articles. The articles are commonly flushable. The term "flushable" as used herein refers to materials which are capable of dissolving, dispersing, disintegrating, and/or decomposing in a septic disposal system such as a toilet to provide clearance when flushed down the toilet without clogging the toilet or any other sewage drainage pipe. The fibers and resulting articles may also be aqueous responsive. The term aqueous responsive as used herein means that when placed in water or flushed, an observable and measurable change will result. Typical observations include noting that the article swells, pulls apart, dissolves, or observing a general weakened structure.

The tensile strength of a starch fibers is approximately 15 Mega Pascal (MPa). The multicomponent fibers of the present invention will have a tensile strength of greater than about 20 MPa, preferably greater than about 35 MPa, and more preferably greater than about 50 MPa. Tensile strength is measured using an Instron following a procedure described by ASTM standard D 3822-91 or an equivalent test.

The multicomponent fibers of the present invention are not brittle and have a toughness of greater than 2 MPa. Toughness is defined as the area under the stress-strain curve where the specimen gauge length is 25 mm with a strain rate of 50 mm per minute. Elasticity or extensible of the fibers may also be desired.

The multicomponent fibers of the present invention may be thermally bondable if enough polymer is present. Thermally bondable fibers are required for the pressurized heat and thru-air heat bonding methods. Thermally bondable is typically achieved when the polymer is present at a level of greater than about 15% preferably greater than about 30%, most preferably greater than about 40%, and most preferably greater than about 50% by weight of the fiber. Consequently, if a very high starch content is in the sheath, the fiber may exhibit a decreased tendency toward thermal bondablility.

The nonwoven products produced from the multicomponent fibers will also exhibit certain mechanical properties, particularly, strength, flexibility, softness, and absorbency. Measures of strength include dry and/or wet tensile strength. Flexibility is related to stiffness and can attribute to softness.

Softness is generally described as a physiologically perceived attribute which is related to both flexibility and texture. Absorbency relates to the products' ability to take up fluids as well as the capacity to retain them.

(4) Processes

The first step in producing a multicomponent fiber is the compounding or mixing step. In the compounding step, the raw materials are heated, typically under shear. The shearing in the presence of heat will result in a homogeneous melt with proper selection of the composition. The melt is then placed in an extruder where fibers are formed. A collection of fibers is combined together using heat, pressure, chemical binder, mechanical entanglement, and combinations thereof resulting in the formation of a nonwoven web. The nonwoven is then assembled into an article.

Compounding

The objective of the compounding step is to produce a homogeneous melt composition comprising the starch, polymer, and/or plasticizer. If a constituent is being produced that is only starch or polymer and not both, the compounding step will be modified to account for the desired composition. Preferably, the melt composition is homogeneous, meaning that a uniform distribution is found over a large scale and that no distinct regions are observed.

The resultant melt composition should be essentially free of water to spin fibers. Essentially free is defined as not creating substantial problems, such as causing bubbles to form which may ultimately break the fiber while spinning. Preferably, the free water content of the melt composition is less than about 1%, more preferably less than about 0.5%, and most preferably less than 0.1%. The total water content includes the bound and free water. To achieve this low water content, the starch and polymers may need to be dried before processed and/or a vacuum is applied during processing to remove any free water. Preferably, the thermoplastic starch is dried at 60° C. before spinning.

In general, any method using heat, mixing, and pressure can be used to combine the polymer, starch, and/or plasticizer. The particular order or mixing, temperatures, mixing speeds or time, and equipment are not critical as long as the starch does not significantly degrade and the resulting melt is homogeneous.

A method of mixing for a starch and two polymer blend is as follow:

1. The polymer having a higher melting temperature is heated and mixed above its melting point. Typically, this is 30°–70° C. above its melting temperature. The mixing time is from about 2 to about 10 minutes, preferably around 5 minutes. The polymer is then cooled, typically to 120°–140° C.
2. The starch is fully destructurized. This starch can be destructurized by dissolving in water at 70°–100° C. at a concentration of 10–90% starch depending upon the molecular weight of the starch, the desired viscosity of the destructurized starch, and the time allowed for destructurizing. In general, approximately 15 minutes is sufficient to destructurize the starch but 10 minutes to 30 minutes may be necessary depending upon conditions. A plasticizer can be added to the destructurized starch if desired.
3. The cooled polymer from step 1 and the destructurized starch from step 2 are then combined. The polymer and starch can be combined in an extruder or a batch mixer with shear. The mixture is heated, typically to approximately 120°–140° C. This results in vaporization of any water. If desired to flash off all water, the mixture should be mixed until all of the water is gone. Typically, the mixing in this step is from about 2 to about 15 minutes, typically it is for approximately 5 minutes. A homogenous blend of starch and polymer is formed.
4. A second polymer is then added to the homogeneous blend of step 3. This second polymer may be added at room temperature or after it has been melted and mixed. The homogeneous blend from step 3 is continued to be mixed at temperatures from about 100° C. to about 170° C. The temperatures above 100° C. are needed to prevent any moisture from forming. If not added in step 2, the plasticizer may be added now. The blend is continued to be mixed until it is homogeneous. This is observed by noting no distinct regions. Mixing time is generally from about 2 to about 10 minutes, commonly around 5 minutes.

Another method of mixing for a starch and plasticizer blend is as follows:

1. The starch is destructured by addition of a plasticizer. The plasticizer, if solid such as sorbitol or mannitol, can be added with starch (in powder form) into a twin-screw extruder. Liquids such as glycerine, can be combined with the starch via volumetric displacement pumps.
2. The starch is fully destructurized by application of heat and shear in the extruder. The starch and plasticizer mixture is typically heated to 120–180° C. over a period of from about 10 seconds to about 15 minutes, until the starch gelatinizes.
3. A vacuum can applied to the melt in the extruder, typically at least once, to remove free water. Vacuum can be applied, for example, approximately two-thirds of the way down the extruder length, or at any other point desired by the operator.
4. Alternatively, multiple feed zones can be used for introducing multiple plasticizers or blends of starch.
5. Alternatively, the starch can be premixed with a liquid plasticizer and pumped into the extruder.

As will be appreciated by one skilled in the art of compounding, numerous variations and alternate methods and conditions can be used for destructuring the starch and formation of the starch melt including, without limitation, via feed port location and screw extruder profile.

A suitable mixing device is a multiple mixing zone twin screw extruder with multiple injection points. The multiple injection points can be used to add the destructurized starch and the polymer. A twin screw batch mixer or a single screw extrusion system can also be used. As long as sufficient mixing and heating occurs, the particular equipment used is not critical.

An alternative method for compounding the materials is by adding the plasticizer, starch, and polymer to an extrusion system where they are mixed in progressively increasing temperatures. For example, in a twin screw extruder with six heating zones, the first three zones may be heated to 90°, 120°, and 130° C., and the last three zones will be heated above the melting point of the polymer. This procedure results in minimal thermal degradation of the starch and for the starch to be fully destructed before intimate mixing with the thermoplastic materials.

Another process is to use a higher temperature melting polymer and inject the starch at the very end of the process. The starch is only at a higher temperature for a very short amount of time which is not enough time to burn.

An example of compounding destructured thermoplastic starch would be to use a Werner & Pfleiderer (30 mm diameter 40:1 length to diameter ratio) co-rotating twin-screw extruder set at 250 RPM with the first two heat zones set at 50° C. and the remaining five heating zones set 150° C. A vacuum is attached between the penultimate and last heat section pulling a vacuum of 10 atm. Starch powder and plasticizer (e.g., sorbitol) are individually fed into the feed throat at the base of the extruder, for example using mass-loss feeders, at a combined rate of 30 lbs/hour (13.6 kg/hour) at a 60/40 weight ratio of starch/plasticizer. Processing aids can be added along with the starch or plasticizer. For example, magnesium separate can be added, for example, at a level of 0–1%, by weight, of the thermoplastic starch component.

Spinning

The present invention utilizes the process of melt spinning. In melt spinning, there is no mass loss in the extrudate. Melt spinning is differentiated from other spinning, such as wet or dry spinning from solution, where a solvent is being eliminated by volatilizing or diffusing out of the extrudate resulting in a mass loss.

Spinning will occur at 120° C. to about 230°, preferably 185° to about 190°. Fiber spinning speeds of greater than 100 meters/minute are required. Preferably, the fiber spinning speed is from about 1,000 to about 10,000 meters/minute, more preferably from about 2,000 to about 7,000 meters/minute, and most preferably from about 2,500 to about 5,000 meters/minute. The polymer composition must be spun fast to avoid brittleness in the fiber.

Continuous fibers can be produced through spunbond methods or meltblowing processes or non-continuous (staple fibers) fibers can be produced. The various methods of fiber manufacturing can also be combined to produce a combination technique.

The homogeneous blend can be melt spun into multicomponent fibers on conventional melt spinning equipment. The equipment will be chosen based on the desired configuration of the multicomponent. Commercially available melt spinning equipment is available from Hills, Inc. located in Melbourne, Fla. The temperature for spinning range from about 100° C. to about 230° C. The processing temperature is determined by the chemical nature, molecular weights and concentration of each component. The fibers spun can be collected using conventional godet winding systems or through air drag attenuation devices. If the godet system is used, the fibers can be further oriented through post extrusion drawing at temperatures from about 50° to about 140° C. The drawn fibers may then be crimped and/or cut to form non-continuous fibers (staple fibers) used in a carding, airlaid, or fluidlaid process.

For example, a suitable process for spinning bicomponent, sheath/core fiber with a destructured starch sheath and a polypropylene core is as follows. The destructured starch component extruder profile may be 80° C., 150° C. and 150° C. in the first three zones of a three heater zone extruder with a starch composition similar to Example 7. The transfer lines and melt pump heater temperatures may be 150° C. for the starch component. The polypropylene component extruder temperature profile may be 180° C., 230° C. and 230° C. in the first three zones of a three heater zone extruder. The transfer lines and melt pump can be heated to 230° C. In this case the spinneret temperature can range from 180° C. to 230° C.

In the process of spinning fibers, particularly as the temperature is increased above 105° C., typically it is desirable for residual water levels to be 1%, by weight of the fiber, or less, alternately 0.5% or less, or 0.15% or less.

(5) Articles

The multicomponent fibers may be converted to nonwovens by different bonding methods. Continuous fibers can be formed into a web using industry standard spunbond type technologies while staple fibers can be formed into a web using industry standard carding, airlaid, or wetlaid technologies. Typical bonding methods include: calendar (pressure and heat), thru-air heat, mechanical entanglement, hydrodynamic entanglement, needle punching, and chemical bonding and/or resin bonding. The calendar, thru-air heat, and chemical bonding are the preferred bonding methods for the starch and polymer multicomponent fibers. Thermally bondable fibers are required for the pressurized heat and thru-air heat bonding methods.

The multicomponent fibers of the present invention may also be bonded or combined with other synthetic or natural fibers to make nonwoven articles. The synthetic or natural fibers may be blended together in the forming process or used in discrete layers. Suitable synthetic fibers include fibers made from polypropylene, polyethylene, polyester, polyacrylates, and copolymers thereof and mixtures thereof. Natural fibers include cellulosic fibers and derivatives thereof. Suitable cellulosic fibers include those derived from any tree or vegetation, including hardwood fibers, softwood fibers, hemp, and cotton. Also included are fibers made from processed natural cellulosic resources such as rayon.

The multicomponent fibers of the present invention may be used to make nonwovens, among other suitable articles. Nonwoven articles are defined as articles that contains greater than 15% of a plurality of fibers that are continuous or non-continuous and physically and/or chemically attached to one another. The nonwoven may be combined with additional nonwovens or films to produce a layered product used either by itself or as a component in a complex combination of other materials, such as a baby diaper or feminine care pad. Preferred articles are disposable, nonwoven articles. The resultant products may find use in filters for air, oil and water; vacuum cleaner filters; furnace filters; face masks; coffee filters, tea or coffee bags; thermal insulation materials and sound insulation materials; nonwovens for one-time use sanitary products such as diapers, feminine pads, and incontinence articles; biodegradable textile fabrics for improved moisture absorption and softness of wear such as micro fiber or breathable fabrics; an electrostatically charged, structured web for collecting and removing dust; reinforcements and webs for hard grades of paper, such as wrapping paper, writing paper, newsprint, corrugated paper board, and webs for tissue grades of paper such as toilet paper, paper towel, napkins and facial tissue; medical uses such as surgical drapes, wound dressing, bandages, dermal patches and self-dissolving sutures; and dental uses such as dental floss and toothbrush bristles. The fibrous web may also include odor absorbents, termite repellants, insecticides, rodenticides, and the like, for specific uses. The resultant product absorbs water and oil and may find use in oil or water spill clean-up, or controlled water retention and release for agricultural or horticultural applications. The resultant starch fibers or fiber webs may also be incorporated into other materials such as saw dust, wood pulp, plastics, and concrete, to form composite materials, which can be used as building materials such as walls, support beams, pressed boards, dry walls and backings, and ceiling tiles; other medical uses such as casts, splints, and tongue depressors; and in fireplace logs for decorative and/or burning purpose. Preferred articles of the present invention include disposable nonwovens for hygiene and medical applications.

Hygiene applications include such items as wipes; diapers, particularly the top sheet or back sheet; and feminine pads or products, particularly the top sheet.

EXAMPLES

The examples below further illustrate the present invention. The starch used in the examples below are StarDri 100, StaDex 10, StaDex 65, all from Staley. The polycaprolactone (PCL) is Tone 767 purchased from Union Carbide. The polyethylene is Aspin 6811A purchased from Dow and the polypropylene is Achieve 3854 purchased from Exxon.

Example 1

Sheath-Core Bicomponent Fiber

The blend for the core is compounded using 70 parts StarDri 100, 10 parts polyethylene and 30 parts sorbital. The blend for the sheath is compounded using 67 parts low density polyethylene, 19 parts StarDri 100 starch, 10 parts PCL and 4 parts glycerol. Each ingredient is added concurrently to an extrusion system where they are mixed in progressively increasing temperatures. This procedure minimizes the thermal degradation to the starch that occurs when the starch is heated above 180° C. for significant periods of time. This procedure also allows the starch to be fully destructured before intimate mixing with the thermoplastic materials.

Example 2

Sheath-Core Bicomponent Fiber

The blend for the sheath contains polypropylene. The blend for the core is compounded as in Example 1 using 66 parts polypropylene, 20 parts StarDri 100, 9 parts PCL, and 5 parts glycerol.

Example 3

Hollow Eight Segmented Pie Bicomponent Fiber

The blend for the first segment contains polyethylene. The blend for the second component is compounded as in Example 1 using 70 parts StarDri 100, 10 parts polyethylene and 30 parts sorbital.

Example 4

Sheath-Core Bicomponent Fiber

The blend for the core contains polyethylene. The blend for the sheath is compounded as in Example 1 using 30 parts StaDex 10, 15 parts polypropylene, 45 parts polyethylene and 15 parts sorbital.

Example 5

Side-by-Side Bicomponent Fiber

The blend for the firsts segment contains polypropylene. The blend for the second component is compounded as in Example 1 using 70 parts StarDri 100 and 30 parts sorbital.

Example 6

Sheath-Core Bicomponent Fiber

The blend for the sheath segment contains polyethylene. The blend for the core is compounded as in Example 1 using 50 parts StaDex 15 and 50 parts sorbital.

Example 7

Sheath-Core Bicomponent Fiber

The blend for the core contains polypropylene. The blend for the sheath is compounded as in Example 1 using 70 parts StarDri 100 and 30 parts sorbital. After the bicomponent fiber is spun, the starch containing sheath is dissolved in water. The remaining polypropylene fiber can then be used to make a nonwoven web. The dissolved starch and water can be recycled and used again.

Example 8

Islands-in-the-Sea Fiber

The "islands" in the multicomponent fiber contain Dow Primacor 5980I. The matrix blend is compounded according to Example 1 with 10 parts Dow Primacor 5980I, 70 parts StarDri 100 and 30 parts sorbitol.

Example 9

Side-by-Side

Fibers can be produced by melt spinning a composition comprising 36 parts polypropylene, 37 parts StarDri 100 starch, 18 parts PCL and 9 parts glycerol. The second component comprises 48 parts polypropylene, 33 parts Star Dri 100 starch, 14 parts PCL, and 5 parts glycerol. Both component are compounded according to Example 1.

Example 10

Segmented Pie

One component of the fiber can be produced by melt spinning a composition comprising 20 parts polypropylene, 20 parts polyethylene, 20 parts EAA, 25 parts StaDex 10, and 15 parts sorbitol. The second component can be produced by melt spinning a composition comprising 80 parts polypropylene, 10 parts PCL, 10 parts StaDex 15, and 5 parts sorbitol. Both component are compounded according to Example 1.

Example 11

Hollow Non-Continuous Sheath-Core

The sheath can be produced by melt spinning a composition comprising 50 parts PVA, 30 parts StaDex 65, and 20 parts mannitol. The hollow core comprises 50 parts StaDex 65 and 50 parts sorbitol.

Example 12

Three Part Ribbon

One component of the ribbon fiber is be produced by melt spinning a composition comprising 20 parts PVA, 60 parts StaDex 10, and 20 parts mannitol. This component is located on either side of the middle component which comprises 70 parts StarDri 100 and 30 parts glycerin.

Example 13

Hollow Segmented Pie

One segment of the fiber can be produced by melt spinning a composition comprising 50 parts Nylon 6, 30 parts StaDex 15, and 20 parts suitable diluent for lowering the melting temperature of Nylon 6. The other segment will comprise 30 parts Nylon 12, 50 parts StaDex 15, and 20 parts of a suitable diluent for lowering the melting temperature of Nylon 6.

While particular examples were given, different combinations of materials, ratios, and equipment such as counter rotating twin screw or high shear single screw with venting could also be used.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of the invention.

What is claimed is:

1. A multicomponent fiber having a configuration selected from the group consisting of sheath-core, islands-in-the-sea, ribbon, segmented pie, side-by-side, and combination thereof; wherein each component of the multicomponent fiber comprises a material selected from group consisting of destructurized starch, thermoplastic polymer having a molecular weight of less than 500,000 g/mol, and combinations thereof.

2. The multicomponent fiber of claim 1 wherein one component comprises:
   a. destructurized starch,
   b. a thermoplastic polymer having a molecular weight of less than about 500,000, and
   c. a plasticizer.

3. The multicomponent fiber of claim 1 wherein one component comprises destructurized starch and a second component comprises a thermoplastic polymer having a molecular weight of less than about 500,000 g/mol.

4. The multicomponent fiber of claim 1 wherein the fiber has a diameter of less than 200 micrometers.

5. The multicomponent fiber of claim 1 where the fiber is splittable.

6. The multicomponent fiber of claim 1 wherein the fiber is thermally bondable.

7. A bicomponent fiber having a sheath-core configuration wherein the sheath comprises destructurized starch and a plasticizer and the core comprises a thermoplastic polymer having a molecular weight of less than 500,000 g/mol.

8. A bicomponent fiber having a sheath-core configuration wherein the sheath comprises a thermoplastic polymer having a molecular weight of less than 500,000 g/mol and the core comprises destructurized starch and a plasticizer.

* * * * *